United States Patent
Petit

(10) Patent No.: US 9,364,842 B2
(45) Date of Patent: Jun. 14, 2016

(54) PUMP FOR DISPENSING A FLUID MATERIAL

(75) Inventor: Ludovic Petit, Vitot (FR)

(73) Assignee: APTAR FRANCE SAS, Le Neubourg (FR)

( * ) Notice: Subject to any disclaimer, the term of this patent is extended or adjusted under 35 U.S.C. 154(b) by 0 days.

(21) Appl. No.: 14/005,740

(22) PCT Filed: Mar. 22, 2012

(86) PCT No.: PCT/FR2012/050595
§ 371 (c)(1),
(2), (4) Date: Sep. 17, 2013

(87) PCT Pub. No.: WO2012/131234
PCT Pub. Date: Oct. 4, 2012

(65) Prior Publication Data
US 2014/0001213 A1 Jan. 2, 2014

(30) Foreign Application Priority Data
Mar. 25, 2011 (FR) ...................................... 11 52488

(51) Int. Cl.
*B65D 88/54* (2006.01)
*B05B 11/00* (2006.01)
*A61M 15/08* (2006.01)

(52) U.S. Cl.
CPC ........... *B05B 11/3001* (2013.01); *B05B 11/304* (2013.01); *B05B 11/3004* (2013.01); *B05B 11/3016* (2013.01); *B05B 11/3063* (2013.01); *B05B 11/3074* (2013.01); *B05B 11/3094* (2013.01); *A61M 15/08* (2013.01); *B05B 11/3047* (2013.01)

(58) Field of Classification Search
USPC ............................................ 222/321.6–321.9
See application file for complete search history.

(56) References Cited

U.S. PATENT DOCUMENTS 7,775,404 B2 * 8/2010 Pardonge et al. .......... 222/321.7
7,870,978 B2 * 1/2011 Pardonge et al. .......... 222/321.7
(Continued)

FOREIGN PATENT DOCUMENTS

FR           2 838 783 A1    10/2003
WO    WO 03086650 A1 * 10/2003
(Continued)

OTHER PUBLICATIONS

English translation of the International Preliminary Report on Patentability for PCT/FR2012/050595.

*Primary Examiner* — Donnell Long
(74) *Attorney, Agent, or Firm* — Sughrue Mion, PLLC

(57) ABSTRACT

A fluid dispenser pump including a first piston, a second piston, and a dispenser head with a dispenser orifice, for actuating the pump, a shutter arranged upstream from the dispenser orifice, the shutter movable between closed and open positions. The second piston is formed outside a hollow part and is slidable inside the dispenser head. The first piston is slidable inside the hollow part, the hollow part including an axial opening defined by a radial edge through which passes a stem portion of the shutter. The stem portion is between a proximal radial shoulder and a distal radial shoulder of the shutter, the shutter being moved from its closed position to its open position by the radial edge of the hollow part co-operating with the distal radial shoulder, and being moved from its open position to its closed position by the radial edge co-operating with the proximal radial shoulder.

12 Claims, 2 Drawing Sheets

(56) References Cited

U.S. PATENT DOCUMENTS

| | | | |
|---|---|---|---|
| 2001/0020627 A1* | 9/2001 | Meshberg | 222/1 |
| 2002/0030069 A1* | 3/2002 | Auer | 222/481.5 |
| 2003/0197031 A1* | 10/2003 | Petit | 222/321.9 |
| 2004/0026457 A1* | 2/2004 | Petit | 222/321.2 |
| 2007/0131799 A1* | 6/2007 | Le Maner et al. | 239/483 |
| 2011/0114676 A1 | 5/2011 | Margheritis et al. | |

FOREIGN PATENT DOCUMENTS

| | | |
|---|---|---|
| WO | 2010/004224 A2 | 1/2010 |
| WO | WO 2010004224 A2 * | 1/2010 |

* cited by examiner

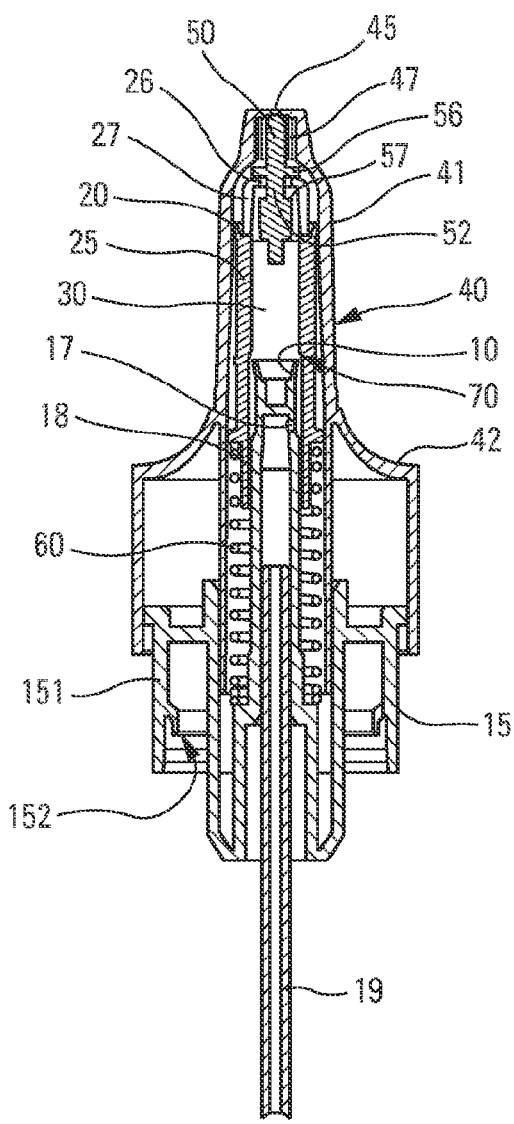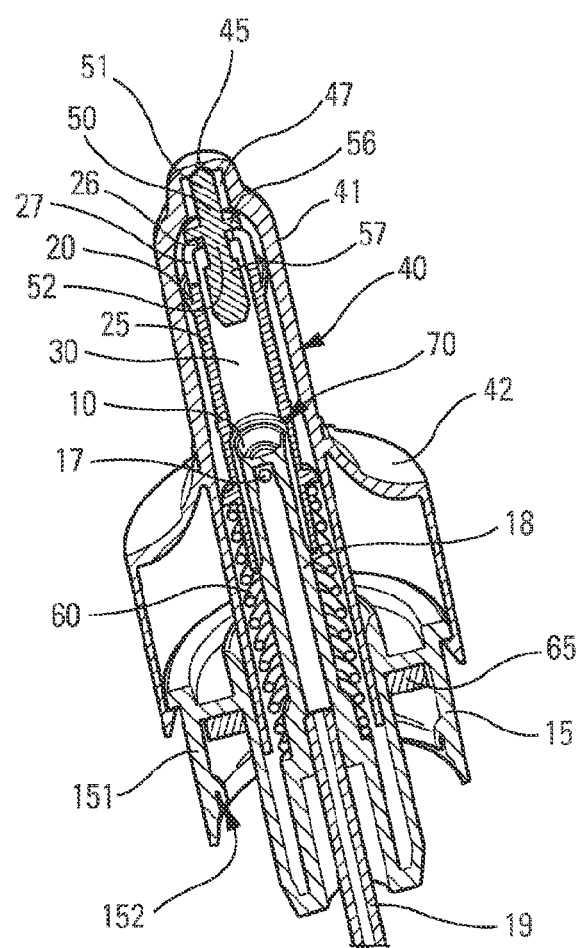
Fig. 1
Fig. 2

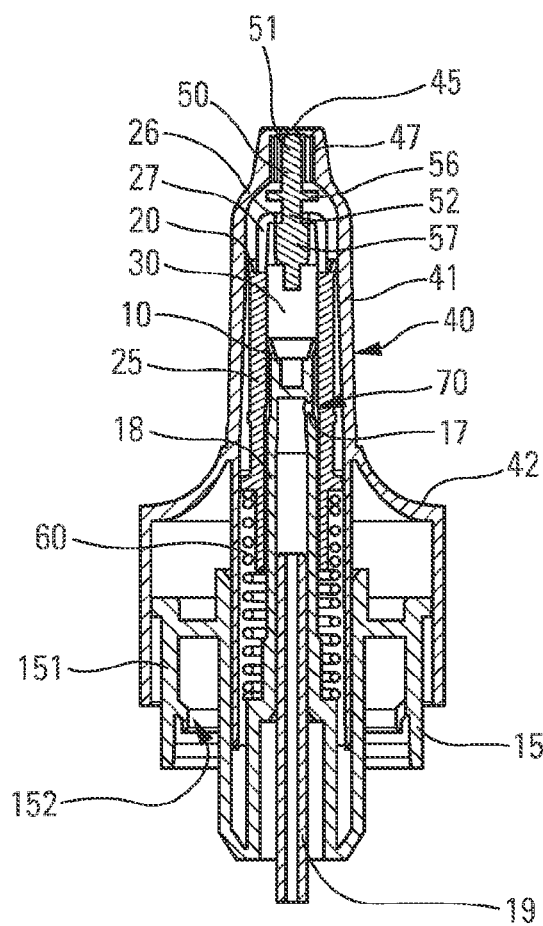
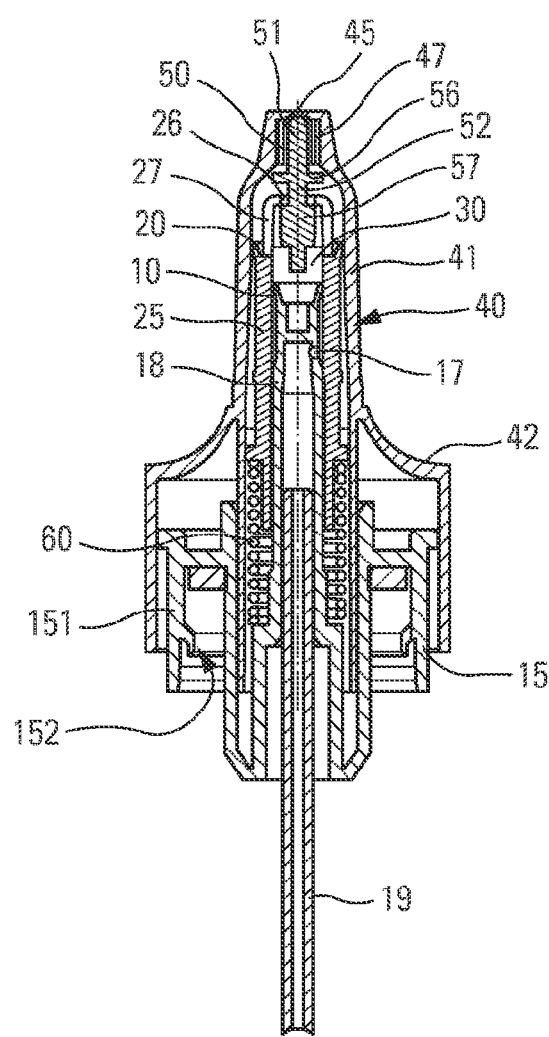
Fig. 3
Fig. 4

PUMP FOR DISPENSING A FLUID MATERIAL

CROSS REFERENCE TO RELATED APPLICATIONS

This application is a National Stage of International Application No. PCT/FR2012/050595, filed on Mar. 22, 2012, which claims priority from French Patent Application No. 11 52488, filed on Mar. 25, 2011, the contents of all of which are incorporated herein by reference in their entirety.

The present invention relates to a fluid dispenser pump and to a fluid dispenser device including such a pump.

Fluid dispenser pumps are well known in the state of the art, in particular for dispensing fluids, liquids, or pastes in the fields of cosmetics, perfumery, or pharmacy. They generally include a piston that slides in a pump body, more particularly in a pump chamber provided in the pump body, and that is adapted to dispense a dose of fluid each time the pump is actuated. The pump chamber generally includes an inlet valve so as to make it possible to define the dose of fluid expelled on each actuation. In addition, in particular with pharmaceuticals, pumps sometimes incorporate shutters for their dispenser orifices, so as to avoid any contamination of the fluid between two actuations.

A problem that occurs with that type of pump relates to priming. Before the pump is actuated for the first time, the pump chamber is full of air, and it is thus necessary to expel all of the air so as to enable said pump chamber to be filled with fluid, and so as to enable accurate and reproducible metering each time the pump is actuated. Priming is made all the more complicated when the pump includes a shutter. It is difficult to expel the air contained in the pump chamber out from said pump chamber, in particular because of the presence of said shutter.

Another problem that can occur with fluid dispenser pumps relates to the quality of the spray, when said pump is a spray pump. Particularly when a shutter is provided for the dispenser orifice, the quality and the characteristics of the spray during expulsion depend on said shutter. Unfortunately, since most shutters are moved by the fluid pressure created during actuation, actuations with different intensities or axial forces can cause the characteristics of the spray to change. In particular in pumps in which the shutter moves axially away from the dispenser orifice during actuation of the pump, too great a displacement of said shutter risks causing a loss in the quality of the spray, and consequently poor dispensing of the dose. Furthermore, actuation with insufficient force may lead to a dose being dispensed in part only.

Another problem that can also occur with fluid dispenser pumps relates to the risk of the pump becoming blocked. In particular, this risk can occur with so-called "airless" suction pumps if the suction in the fluid reservoir exceeds the suction that the pump or metering chamber is capable of generating when the pump returns to its rest position after actuation. The inlet valve of the pump chamber can thus become blocked, thereby blocking the pump as a whole. In this event, the natural suction capability of the pump is insufficient to counter the suction from the reservoir, if the suction level is not always relayed to the pump chamber after each actuation. Unfortunately, as a pump is used, some of its component parts, generally those made of plastics material that is more or less rigid, risk deforming naturally under the effect of the suction, and are thus likely to generate this disadvantageous increase in reservoir suction relative to pump-chamber suction.

Documents WO 2010/004224 and FR 2 838 783 describe prior-art devices.

An object of the present invention is to provide a fluid dispenser pump that does not have the above-mentioned drawbacks.

More particularly, an object of the present invention is to provide a fluid dispenser pump that avoids any risk of the pump becoming blocked, in particular by avoiding an excessive increase in reservoir suction relative to pump-chamber suction.

Another object of the present invention is to provide a fluid dispenser pump that makes it possible to provide priming that is safe and reliable, in simple and inexpensive manner.

Another object of the present invention is to provide a fluid dispenser pump that guarantees spraying each time the pump is actuated, regardless of the force exerted by the user on said pump during its actuation, and that guarantees that the entire dose is dispensed on each actuation.

The present invention also provides a fluid dispenser pump that is simple and inexpensive to manufacture and to assemble.

The present invention thus provides a fluid dispenser pump comprising a first piston, a second piston, and a dispenser head, provided with a dispenser orifice, for actuating said pump, a shutter being arranged upstream from said dispenser orifice, said shutter being movable between closed and open positions of said dispenser orifice, said second piston being formed outside a hollow part and being slidable inside said dispenser head, said first piston being slidable inside said hollow part, said hollow part including an axial opening that is defined by a radial edge through which there passes a stem portion of the shutter, said stem portion being defined between a proximal radial shoulder and a distal radial shoulder of the shutter, said shutter being moved from its closed position to its open position by said radial edge of said hollow part co-operating with said distal radial shoulder, and being moved from its open position to its closed position by said radial edge co-operating with said proximal radial shoulder.

Advantageously, said first piston forms an inlet valve, and said shutter forms an outlet valve of a pump chamber that is defined by said first and second pistons.

Advantageously, during actuation, said hollow part moves relative to said dispenser head and relative to said shutter.

Advantageously, said shutter includes a closure portion that slides in a sleeve that is arranged in the dispenser head upstream from the dispenser orifice, said sleeve including a spray profile.

Advantageously, a single spring urges said pistons towards their rest positions, and said shutter towards its closed position.

Advantageously, said spring does not come into any contact with the fluid.

Advantageously, said first piston is made integrally with a fastener element, such as a snap-fastenable, crimpable, or screw-fastenable ring, that is adapted to fasten said pump on a fluid reservoir.

Advantageously, said first piston is secured to a hollow rod that is connected to a dip tube that extends into said reservoir.

Advantageously, in the proximity of said radial edge, said hollow part includes a fluid passage, enabling the fluid to pass from the inside to the outside of said hollow part.

The present invention also provides a fluid dispenser device comprising a fluid reservoir and a pump as described above.

Advantageously, said pump is fastened on a reservoir by a snap-fastener ring that includes a peripheral skirt and at least one snap-fastener profiles that projects radially inwards from said peripheral skirt, each snap-fastener profile including an axial wall that is spaced apart from said peripheral skirt so as to form a hollow gap, said snap-fastener profile being elastically deformable into said hollow gap.

Other characteristics and advantages of the present invention appear more clearly from the following detailed description thereof, given by way of non-limiting example, and with reference to the accompanying drawing, in which:

FIG. 1 is a diagrammatic section view of a pump in an advantageous embodiment of the present invention, shown in its rest position;

FIG. 2 is a diagrammatic and partially cut-away perspective view of the pump of FIG. 1;

FIG. 3 is a view similar to the view in FIG. 1, during actuation; and

FIG. 4 is a view similar to the view in FIG. 1, at the end of actuation;

With reference to the figures, a fluid dispenser device includes a dispenser pump that is mounted on a reservoir (not shown) by means of a fastener ring 15, advantageously with a sealing gasket 65 interposed therebetween. The fastener ring may be a crimping, screw-fastener, or snap-fastener ring. A dispenser head 40, that includes a dispenser orifice 45, is provided so as to actuate said pump 10. The dispenser head may be a nasal head, as shown in the drawings, with an elongate axial portion 41 for penetrating into the user's nostril, the dispenser orifice thus being at the downstream end of said elongate portion of the head. A wide actuation portion 42 is provided so as to enable the user to press fingers on said head so as to actuate the pump. Advantageously, the dispenser orifice is provided with a spray profile so as to dispense the fluid in a fine spray.

The dispenser pump includes a first piston 10 and a second piston 20, each of which slides between its respective rest and actuated positions. The second piston 20 is formed outside a hollow part 25, and slides inside said dispenser head 40. The first piston 10 is formed at the end of a hollow rod 18 and slides inside said hollow part 25 that defines said second piston 20. The first piston 10 is stationary relative to the fastener ring 15 and thus relative to the reservoir. In an advantageous variant shown in the drawings, the first piston 10 is formed integrally with said fastener ring 15. The pump further includes a shutter 50 that is arranged directly upstream from the dispenser orifice 45, and that co-operates with said dispenser orifice by being movable between a closed position of the dispenser orifice 45 and an open position thereof. The dispenser orifice 45 makes it possible to dispense fluid out from the device, and the purpose of the shutter 50 is to close the orifice between two actuations, in particular so as to avoid the fluid contained in the device being contaminated by contaminants present in the atmosphere.

Advantageously, the pump includes only one spring 60, which is adapted to return the pistons 10, 20 to their rest positions and the shutter 50 to its closed position after each actuation. The spring 60 advantageously does not come into any contact with the fluid, thereby eliminating any risk of spoiling the fluid in question. The spring 60 advantageously co-operates with said hollow part 25 that forms the second piston 20. The shutter 50 advantageously slides axially between its open and closed positions in a sleeve 47 provided in the end of the actuator head 40. A spray profile is preferably formed in said sleeve 47 so as to enable the fluid to swirl while being expelled, so as to form a spray. Thus, the spray profile is not affected by the movement of the shutter towards its open position, thereby guaranteeing good spraying.

Advantageously, the hollow rod 18 of the first piston 10 defines a channel that extends towards the reservoir. A dip tube 19 for extending to the bottom of the reservoir so as to dispense all of the fluid contained therein can also be connected to said hollow rod 18, or it can be made integrally therewith. The hollow rod may be formed integrally with said fastener ring 15. The hollow rod 18 is advantageously blind, with a transverse passage 17 to enable fluid coming from the reservoir to pass from the inside of said hollow rod to the outside thereof. The connection between the hollow rod 18 and the hollow part 25 is leaktight in all positions, so as to avoid fluid leaks, e.g. towards the spring 60.

A pump chamber 30 is defined between said first and second pistons 10, 20, said shutter 50, and an inlet valve 70. The pump chamber 30 is thus arranged in the dispenser head 40, directly upstream from the dispenser orifice 45. The shutter 50 thus forms the outlet valve of the pump chamber, while simultaneously forming the closure element for closing the dispenser orifice. The inlet valve 70 is advantageously formed by said first piston 10 that, in the open position of said inlet valve, co-operates in non-leaktight manner with a wider-diameter portion of said hollow part 25. In the rest position visible in FIGS. 1 and 2, the first piston 10 is arranged at the larger-diameter portion of the hollow part 25, such that it does not co-operate in leaktight manner with said hollow part 25. The inlet valve 70 is thus open and the fluid coming from the reservoir may thus pass beyond the first piston 10. When the device is actuated, the first piston 10 moves in said hollow part 25 so as to co-operate with the smaller-diameter portion, and thus close the inlet valve 70. From there, the first piston 10 acts as a piston and slides in leaktight manner in said hollow part 25 until it reaches its actuated position. It is only when the first piston returns to its rest position that the inlet valve opens once again so as to enable fluid to pass therethrough.

The hollow part 25 includes a top axial opening through which there passes a stem portion 52 of the shutter 50. The axial opening further defines at least one fluid passage 27, so as to enable the fluid to pass from the inside to the outside of said hollow part 25. The axial opening may be formed by a hole that is formed in the axial end wall of the hollow part 25, such that the radial edge 26 of the hole forms a radial shoulder of said hollow part. The shutter 50 advantageously includes a closure portion 51 that co-operates with the dispenser orifice 45 in the closed position. The shutter 50 also includes a proximal radial shoulder 56 and a distal radial shoulder 57 that are axially offset from each other and that define said stem portion 52 between them. The proximal radial shoulder 56 is closest to the closure portion 51. Thus, as can be seen in the drawings, said radial edge 26 can slide around said stem portion 52 between said two radial shoulders 56, 57. During actuation, the radial edge 26 co-operates with the distal radial shoulder 57 at the end of actuation, so as to move said shutter 50 from its closed position to its open position. After actuation, when the spring 60 returns the hollow part 25 to its rest position, said radial edge 26 co-operates with said proximal radial shoulder 56, so as to return said shutter 50 to its closed position.

Normal operation of the pump is as follows. When the user presses on the dispenser head 40, the proximal radial shoulder 56 of the shutter moves the hollow part 25, compressing the spring 60. The second piston 20 thus slides inside said head, and the first piston 10 slides inside the hollow part 25 so as to close the inlet valve 70. Since the shutter 50 is in its closed position, the pump chamber 30 is thus completely isolated. Since the fluid contained in the pump chamber 30 is incompressible, continuing actuation causes the second piston 20 and thus the hollow part 25 to move relative to said head 40. The hollow part 25 thus moves down inside the head, with the radial edge 26 sliding around said stem portion 52 of the shutter until coming into contact with the distal radial shoulder 57. Continuing actuation from this point thus causes the dispenser orifice 45 to open, the shutter 50 being pulled towards its open position by said radial edge 26 co-operating with said distal radial shoulder 57. The shutter is opened at the end of actuation, thereby preventing any partial dose from being expelled due to an actuation that is not strong enough. If the actuation force exerted by the user is insufficient, the shutter does not open. Once it is ensured that the shutter opens only at the end of an actuation stroke, the entire dose will be dispensed on each actuation. The dose is thus expelled through the dispenser orifice 45, then the spring 60 returns the pump into the rest position, which opens the inlet valve 70, thereby sucking a new dose of fluid into the pump chamber. Advantageously, during actuation, the pressure exerted by the fluid on the proximal radial shoulder 56 of the shutter 50 urges said shutter towards its closed position. This improves the effectiveness of the pump by reinforcing sealing during actuation.

When the user actuates the pump for the first time, and when said pump contains air in the pump chamber 30, the inlet valve and the shutter are closed. Since air is compressible, the first piston 10 can slide in the pump body without the hollow part 25 moving relative to the dispenser head 40, and thus without opening the shutter 50. When the first piston 10 arrives at the fluid passage 27 of the hollow part 25, a passage is created between the pump chamber 30 and the transverse passage 17, thereby making it possible for the air contained in the pump chamber 30 to be expelled towards the hollow rod 18, and thus into the reservoir. After priming, when the pump is returned to its rest position, fluid is sucked into the pump chamber 30. Thereafter, the first piston 10 can no longer reach said fluid passage 27 of the hollow part 25 during normal operation of the pump, i.e. while the fluid is being dispensed, but only at the end of actuation, in the completely actuated position of the first piston 10.

The transverse passage 17 and the fluid passage 27 thus make it possible to connect the pump chamber 30 to the hollow rod 18, and thus to the reservoir, when the first piston 10 reaches its completely actuated position in which the first piston 10 co-operates with the fluid passage 27. This makes it possible to equalize pressure in the pump chamber 30 and in the reservoir after each actuation, and thus prevents the suction in the reservoir increasing relative to the suction in the pump chamber, which would otherwise risk blocking the pump, e.g. by preventing the inlet valve 70 of the pump chamber from opening.

In an advantageous aspect, the fastener ring 15 is of the type that snap-fastens on the outside of the reservoir neck. To this end, it includes a peripheral skirt 151 that is provided on it inside surface with at least one and preferably with a plurality of snap-fastener profiles 152 that project radially inwards. Advantageously, a plurality of profiles 152 of this type are distributed around said ring 15. Each snap-fastener profile 152 advantageously comprises a wall that extends away from said peripheral skirt, preferably sloping radially downwards (in the position shown in the figures), and having an inner radial end that is extended by a wall that is substantially axial, extending downwards (in the position shown in the figures). Thus, a hollow gap is defined between said axial wall and the peripheral skirt of the ring, said axial wall being spaced apart from said peripheral skirt. Thus, each snap-fastener profile 152 is elastically deformable into its respective hollow gap. This configuration makes it easier to snap-fasten the ring 15 on the neck of the reservoir by enabling the snap-fastener profiles 152 to deform. Advantageously, the free end, specifically the bottom end, of the axial wall is beveled, and this encourages said axial wall to deform into said hollow gap during snap-fastening. This configuration of the fastener ring 15 also makes it easier to manufacture by molding, and in particular makes it easier to unmold the snap-fastener profiles 152, which unmolding may take place in two steps. The hollow gap is freed first, and this then makes it possible to deform said profiles during unmolding, without any risk of pulling them off. It should be observed that this particular snap-fastener ring could be used with any type of pump, and that its use is thus not necessarily limited to the pump of the present invention.

The invention is described above with reference to a particular embodiment thereof, but naturally various modifications could be made thereto. In particular, the shapes of the shutter, the pistons, the inlet valve of the pump chamber, or the other elements could be made differently if necessary. Other modifications could also be envisaged by the person skilled in the art, without going beyond the ambit of the present invention, as defined by the accompanying claims.

The invention claimed is:

1. A fluid dispenser pump comprising a first piston, a second piston, and a dispenser head, provided with a dispenser orifice where fluid leaves the dispenser pump, for actuating said pump, a shutter being arranged upstream from said dispenser orifice, said shutter being movable between a closed position, in which the shutter closes the dispenser orifice and an open position, in which the shutter no longer closes the dispenser orifice, said second piston being formed outside a hollow part and being slidable inside said dispenser head, said first piston being slidable inside said hollow part, wherein said hollow part includes an axial opening that is defined by a radial edge through which passes a stem portion of the shutter, said stem portion being defined between a proximal radial shoulder and a distal radial shoulder of the shutter, said shutter being moved from the closed position to the open position by said radial edge of said hollow part co-operating with said distal radial shoulder, and being moved from the open position to the closed position by said radial edge co-operating with said proximal radial shoulder; and said shutter is movable relative to the hollow part.

2. A pump according to claim 1, wherein said first piston forms an inlet valve, and said shutter forms an outlet valve of a pump chamber that is defined by said first and second pistons.

3. A pump according to claim 1, wherein, during actuation, said hollow part moves relative to said dispenser head and relative to said shutter.

4. A pump according to claim 1, wherein said shutter includes a closure portion that slides in a sleeve that is arranged in the dispenser head upstream from the dispenser orifice, said sleeve including a spray profile.

5. A pump according to claim 1, wherein a single spring urges said pistons towards rest positions, and said shutter towards the closed position.

6. A pump according to claim 5, wherein said spring does not come into any contact with the fluid.

7. A pump according to claim 1, wherein said first piston is made integrally with a fastener element that is adapted to fasten said pump on a fluid reservoir.

8. A pump according to claim 1, wherein said first piston is secured to a hollow rod that is connected to a dip tube that extends into said reservoir.

9. A pump according to claim 1, wherein, in the proximity of said radial edge, said hollow part includes a fluid passage, enabling the fluid to pass from the inside to the outside of said hollow part.

10. A fluid dispenser device including a fluid reservoir, the device further comprising a pump according to claim 1.

11. A fluid dispenser device according to claim 10, wherein said pump is fastened on a reservoir by a snap-fastener ring that includes a peripheral skirt and at least one snap-fastener profiles that projects radially inwards from said peripheral skirt, each snap-fastener profile including an axial wall that is spaced apart from said peripheral skirt so as to form a hollow gap, said snap-fastener profile being elastically deformable into said hollow gap.

12. The pump according to claim 1, wherein said first piston is made integrally with a fastener element that is one of a snap-fastenable, crimpable, or screw-fastenable ring and that is adapted to fasten said pump on a fluid reservoir.

\* \* \* \* \*